United States Patent
Freudenthal et al.

(10) Patent No.: US 8,568,465 B2
(45) Date of Patent: Oct. 29, 2013

(54) DEVICE FOR RECHANNELING A CAVITY, ORGAN PATH OR VESSEL

(75) Inventors: Franz Freudenthal, La Paz (BO); Thomas Schmitz-Rode, Aachen (DE)

(73) Assignee: PFM Medical AG, Cologne (DE)

( * ) Notice: Subject to any disclaimer, the term of this patent is extended or adjusted under 35 U.S.C. 154(b) by 846 days.

(21) Appl. No.: 10/592,411

(22) PCT Filed: Mar. 11, 2005

(86) PCT No.: PCT/EP2005/002608
§ 371 (c)(1),
(2), (4) Date: Oct. 6, 2006

(87) PCT Pub. No.: WO2005/087117
PCT Pub. Date: Sep. 22, 2005

(65) Prior Publication Data
US 2007/0203559 A1    Aug. 30, 2007

(30) Foreign Application Priority Data

Mar. 11, 2004 (DE) .......................... 10 2004 012 351

(51) Int. Cl.
*A61F 2/06* (2013.01)
(52) U.S. Cl.
USPC ....... 623/1.11; 623/1.12; 623/1.13; 623/1.15; 623/1.23; 606/200

(58) Field of Classification Search
USPC ............. 623/1.11–1.15, 1.18–1.21, 1.3–1.31; 606/200
See application file for complete search history.

(56) References Cited

U.S. PATENT DOCUMENTS

| | | | | |
|---|---|---|---|---|
| 6,569,147 | B1 * | 5/2003 | Evans et al. | 604/509 |
| 2003/0040772 | A1 * | 2/2003 | Hyodoh et al. | 606/200 |
| 2003/0149472 | A1 * | 8/2003 | Pinchuk et al. | 623/1.13 |
| 2003/0153973 | A1 * | 8/2003 | Soun et al. | 623/1.16 |
| 2004/0098099 | A1 * | 5/2004 | McCullagh et al. | 623/1.15 |
| 2004/0167605 | A1 * | 8/2004 | Elliott | 623/1.13 |
| 2005/0209674 | A1 * | 9/2005 | Kutscher et al. | 623/1.11 |

FOREIGN PATENT DOCUMENTS

WO    WO 02071974 A2 *    9/2002

* cited by examiner

*Primary Examiner* — Gary Jackson
*Assistant Examiner* — Kevin Everage
(74) *Attorney, Agent, or Firm* — Grossman, Tucker, Perreault & Pfleger, PLLC

(57) ABSTRACT

In a device (1) for recanalizing a cavity, organ path or vessel (4) which is at least partially occluded by at least one compressible occlusive object, in particular a thrombus or embolus (3), in the body of a human or animal, using at least one compressible and self-expanding stent (10) having a distal (12) and a proximal end (11), the at least one stent (10) is embodied substantially in a bell shape with a widened distal end (12) and a constricted proximal end (11).

14 Claims, 10 Drawing Sheets

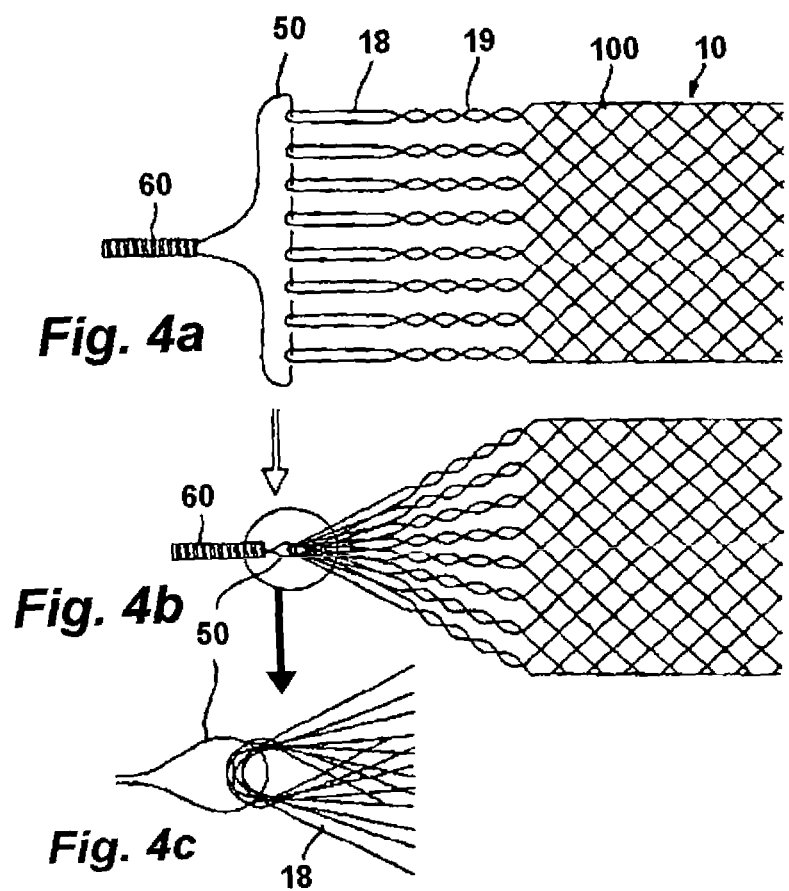

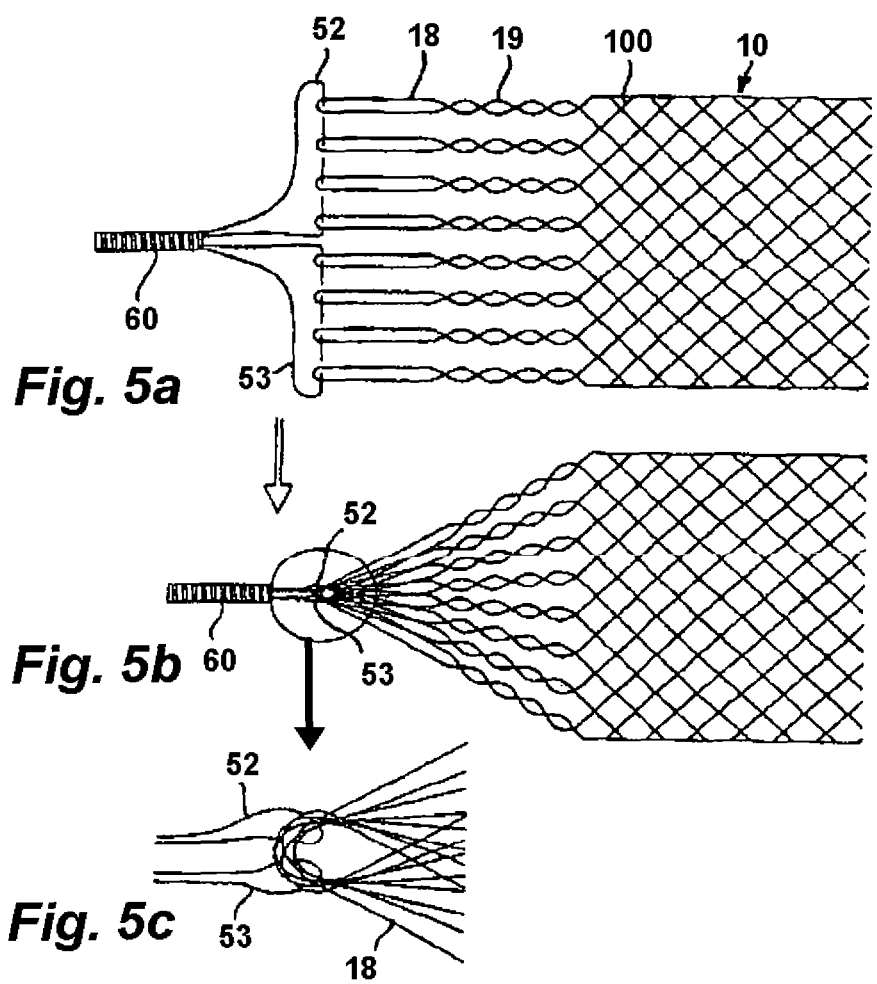

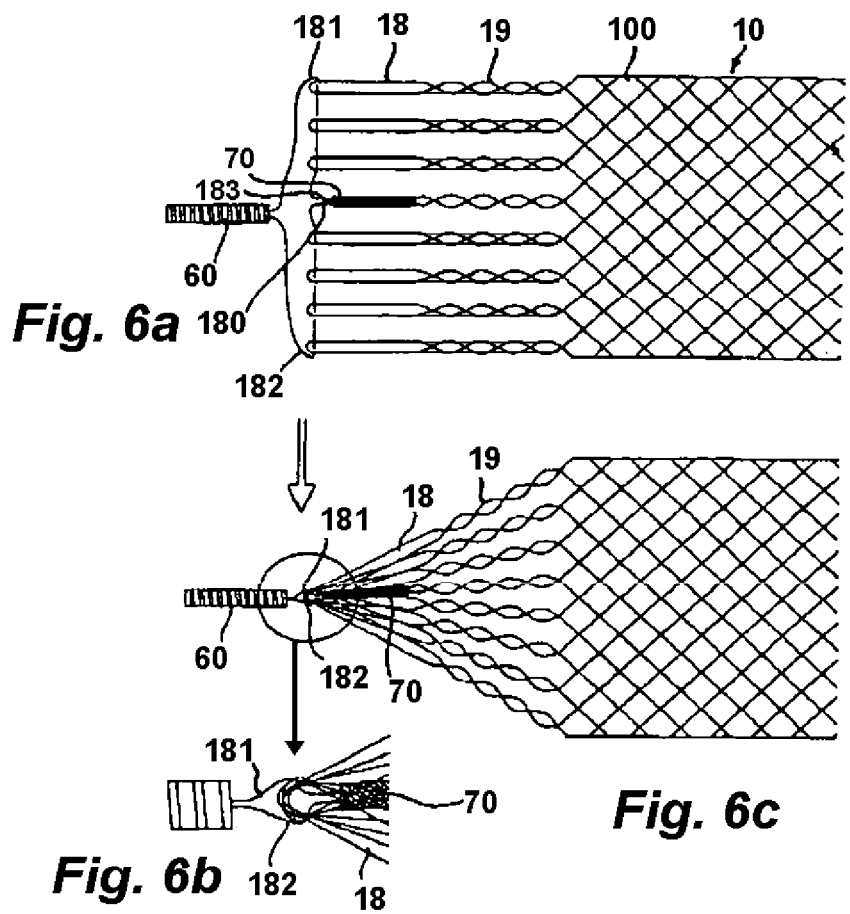

Figure 1:
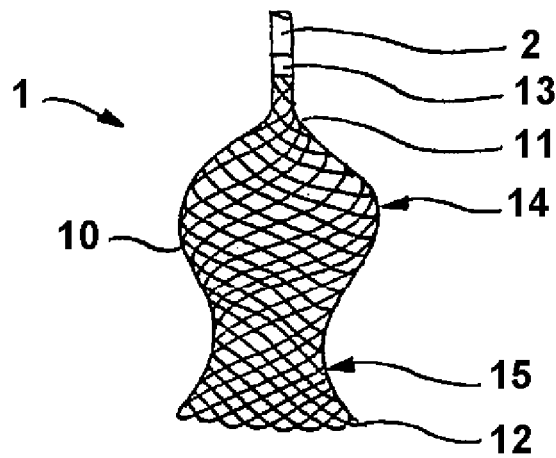

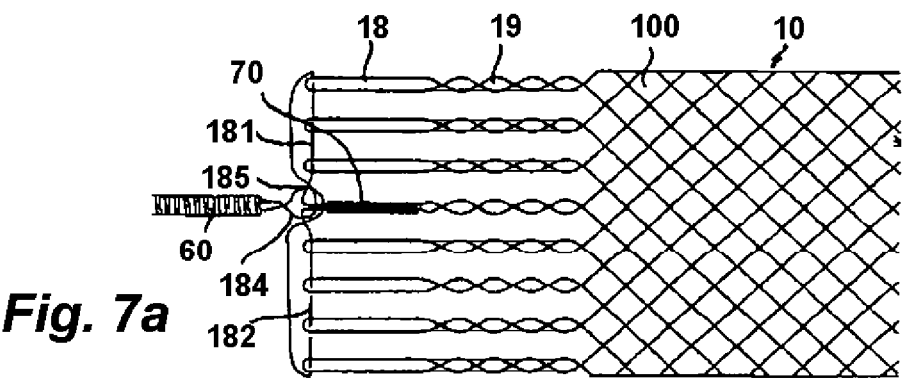
*Fig. 7a*
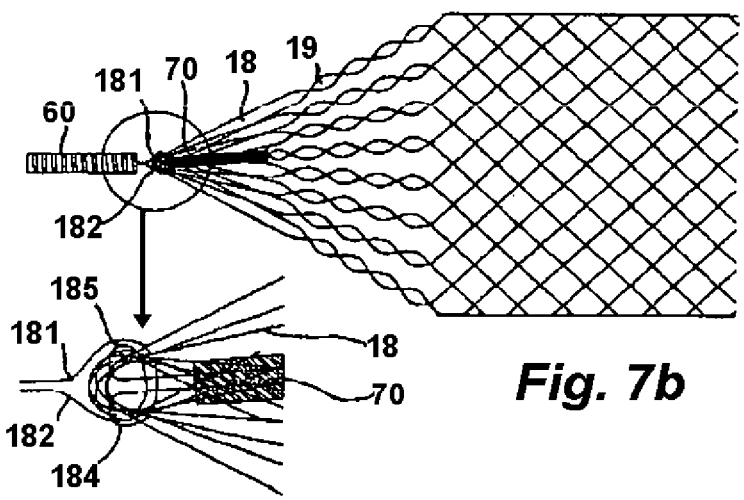
*Fig. 7b*
*Fig. 7c*

DEVICE FOR RECHANNELING A CAVITY, ORGAN PATH OR VESSEL

The invention relates to a device for rechanneling (recanalizing) a cavity, organ path or vessel which is at least partially occluded by at least one compressible occlusive object, in particular a thrombus or embolus, in the body of a human or animal, using at least one compressible and self-expanding stent having a distal and proximal end.

Even in the era of prophylactic anticoagulation, acute pulmonary embolism represents a frequent and often life-threatening event. In cases of massive pulmonary embolism, standard treatment consists of medicinal thrombolysis with streptokinase, urokinase or tissue plasminogen activator. The objective of this is the recanalization of the affected vessel. After these standard treatments have been applied, monitoring by imaging processes such as echocardiography, angiography or computed tomography, shows only slight recanalization after thrombolysis. Despite high-dose thrombolysis, therefore, some patients die of right heart failure.

Alternatively, if thrombolysis is contraindicated, for example in cases of intracranial injury or after operations, or if thrombolsysis has failed, the embolus material can be removed surgically. The intervention using a heart-lung machine places a considerable physical burden on the patient and is associated with a high mortality rate.

Therefore, various devices have been developed to make clearance and recanalization of the vessels easier.

In 1964, Greenfield developed a mechanical instrument with endoscope-like control which extracts pulmonary emboli non-surgically via a venous puncture site. Because of its complicated handling, this suction catheter did not gain widespread acceptance. In 1991, Günther and Schmitz-Rode developed a high-speed catheter system for fragmentation of pulmonary emboli which, because of its technical complexity and the insufficient pulmonary controllability of the catheter, also failed to gain widespread acceptance. A modified pigtail catheter developed by Günther and Schmitz-Rode in 1995 is moved rotatably within the embolic occlusion and in this way effects coarse fragmentation of the embolus material. However, only the soft and fresh embolus material can be fragmented in this way. The modified pigtail catheter fails in cases where there are more solid, organized emboli. In the case of pulmonary arteries filled centrally to peripherally with embolus material, there is little prospect of successful recanalization by fragmentation, since the fragments cannot float off toward the periphery.

These disadvantages do not arise in US 2002/0095161 A1. In this device for extracting stones from the ureter, for example, these stones are captured in a basket having a large opening which expands over half of the surface of the basket and through which stones and stone fragments can pass into the interior of the basket. In addition, the basket has relatively narrow openings which are suitable for holding back the stones and stone fragments. A disadvantage of this has proven to be that, despite the possibility of rotating the basket, the capturing operation is relatively awkward and the stone to be captured does not pass into the basket without any problems.

A similar problem arises in the extraction device according to U.S. Pat. No. 5,779,716 in which a sack-like collecting basket is provided with a wire at its proximal end, which wire keeps the proximal opening of the sack-like collecting basket open in order to assist in the capturing operation.

The prior art also includes extraction devices with coiled wires between which a stone or other foreign body can be captured. An example of this is set out in WO 99/47054. There is a risk here of the stone escaping from the loops while being drawn back in the recovery operation. This applies also to the extraction device disclosed in WO 01/05311 A1 and to the extraction device disclosed in US 2002/0026203 A1.

To remove thrombi from the vascular system, U.S. Pat. No. 5,419,774 A discloses an extraction device whose distal end is provided with a chamber into which the thrombus is drawn by suction. Situated in the chamber there is a separating device which separates that part of the thrombus that is situated in the chamber. A pressurized fluid is delivered in order to carry off the thrombus and the blood collecting with the latter. The structure of the device, however, is relatively complicated since, on the one hand, a means for applying a subatmospheric pressure has to be provided and, on the other hand, a means for delivering a pressurized fluid. Moreover, a means has to be provided for separating the thrombus. These disadvantages also apply to the catheter for working on and removing soft and hard substances for use in invasive microsurgery and vessel treatment according to DE 197 34 890 C1. The area of application of the latter is the removal of tissue or gallstones, for example.

For removal of thrombi, it is also known in the prior art, from US 2002/0026211 A1, to provide a device and a method for filtering of emboli or removal of thrombi from a vessel, in which the device has a vascular filter for trapping the emboli and optionally a thrombectomy element for removal of the thrombus. The vascular filter contains a support ring with one or more hinge areas which are secured near a distal end of a guide wire, and a blood-permeable pouch which is secured on the support ring. The support ring forms the opening of the blood-permeable pouch and holds it open. It is possible to provide two pouches one behind the other, their openings pointing in the same direction, namely in the proximal direction. The first vascular filter captures the thrombus, the second one the remaining emboli. Both vascular filters are retracted into a tube or a catheter together with the thrombus or the emboli. This device proves disadvantageous on account of the support rings in conjunction with the blood-permeable pouch since the hinges provided in the support rings make it expensive to produce. In addition, because of the use of a support ring, the risk of damaging the vessel from which the thrombus or emboli are to be removed is very high, since this support ring is rigid and immovable compared to the vessel and may scrape against the inside wall of the vessel.

A further device for the removal of thrombi is known from U.S. Pat. No. 5,011,488 A. Here, a vascular catheter system comprises an outer flexible tube, an inner flexible tube disposed in the lumen of the outer flexible tube, and an expandable body mounted at a distal end of a third flexible tube itself disposed in the lumen of the inner flexible tube. The inner tube includes an expandable tip which can open to adopt substantially the cross section of a blood vessel. The expandable body is extended through the region of the thrombus and expanded. The thrombus material to be removed is then situated between the two expanded parts, the expanded tip being an inflatable body which bears against the inside wall of the vessel and, when drawn back into the tube, scrapes the thrombus material off from the inside wall of the vessel and carries it toward the expanded body. The inflatable body or balloon fits into the expanded open body and has a truncated cone shape corresponding to the latter. The expanded body has a plurality of spring elements which, after being pushed out of the tube, lead to opening of the expandable tip.

Because of the truncated cone shape, the expanded body is pushed together again when drawn back into the tube. The same happens to the inflatable body or balloon then lying on the inside. This device proves disadvantageous since, when the two bodies are drawn back, the thrombus material located between them can escape again, especially when the inflatable body is compressed, i.e. it is not held securely between the inflatable body and the expandable open truncated cone shaped body.

WO 00/51505 A1 discloses an extraction device with only a distal section which can be widened like a balloon and has intertwined wires covered by a woven fabric. To clear a vessel, the widened end scrapes along the vessel wall and the woven fabric prevents penetration of scraped-off foreign bodies into the device or into the widened section.

DE 692 28 326 T2 discloses an extraction device in which a flexible loop part is covered with a net and secured at its distal end and proximal end on a tensioning wire. By moving the loop part along the tensioning wire, it is possible for the net to assume an open form and a closed form. In this way, a foreign body can be captured in the intertwined loop part covered with net.

WO 00/53120 A1 discloses an extraction device in which two collecting baskets are provided with the openings of the collecting baskets directed toward one another. The distal collecting basket is secured on a rod and is arranged inside the other collecting basket so that it can be drawn inside the latter. The distal collecting basket has a distal contracted end, whereas the proximal collecting basket has a proximal contracted end.

WO02/06465 and US2002/0035394 disclose a device for recanalizing vessels using a stent of cylindrical shape. The cylindrical stent is compressed and, via a catheter, pushed through an embolus and expanded therein. In doing so, its outer surface pushes the embolus material on all sides against the vessel wall, thus recanalizing the vessel. Especially in the case of curved vessels, embolus material may inadvertently slip past the cylindrical stent and lead to further occlusions in the peripheral region.

The object of the present invention is to avoid the aforementioned disadvantages of the prior art and to provide a device for recanalizing cavities and/or organ paths in the body of a human or animal which no longer requires the recovery of compressible objects, a thrombus in particular, occluding a cavity, organ path or a vessel, but still permits effective, non-surgical recanalization especially in the case of partially organized emboli and in cases of extensive embolization of the pulmonary circulation.

The object is achieved with an extraction device in accordance with the preamble of claim 1 in that the at least one stent is embodied substantially in a bell shape with a widened distal end and a constricted proximal end. Developments of the invention are defined in the dependent claims.

Thus, a device for recanalizing a cavity, organ path or vessel in the body of a human or animal is created which assists in pushing the compressible occlusive objects present against the respective wall of the cavity, organ path or vessel in order to express them there. The stent will self-expand on deployment within the region of the object to be compressed. It therefore preferably consists of a shape-memory-effect material. The bell shape of the stent will reliably prevent parts of the compressible occlusive object, embolus material in particular, invading the stent. In contrast to WO02/064065 A2 and US 2002/0035394 A1, the stent may here even be shorter than the object to be compressed without there being the risk of larger sections of the object to be compressed getting inside the stent and therethrough to another site in the human or animal body, where these sections may in turn cause unwanted occlusion of a cavity/organ path or vessel. The stent described in WO02/064065 A2 is cylindrical after expansion and may therefore even be washed away from its site of deployment in the event of a strong blood flow. The bell shape according to the present invention provides for better attachment in the cavity/organ path/vessel in the human or animal body. Here, the distal end of the at least one stent is widened and the proximal end of the at least one stent is constricted. In the region of the distal end of the stent in particular, the slightly flared end will afford particularly good support against a wall of the cavity/vessel/organ path. Owing to its bell shape, the stent is also flared in its proximal region, thus providing good attachment here as well, especially in organ paths and vessels. It is moreover possible to secure the occlusive object to be compressed very well between the two flared end regions of the inventive stent so that it cannot slip away inadvertently either during placement of the stent or thereafter. Adaptation to a curvature of an organ path, vessel or cavity, such as an aortic arch for example, is also easier and more effective owing to the bell shape, the flared distal end and a constricted proximal region in particular having proved advantageous for preventing slippage of an occlusive object to be compressed. The bell shape affords optimum adaptation to the anatomy of the organ path, vessel or cavity concerned, in particular of the right and left main pulmonary artery branch which tapers rapidly, i.e. has a conical shape. Furthermore, proximal inflow of blood is enhanced because the bell shape widens the meshes and smaller particles can be entrained and washed away more rapidly and effectively.

The prior art does not disclose such a bell shape of a stent for the purposes of recanalizing a cavity or organ path or vessel. Rather, EP 0 836 450 B1 discloses a self-expanding stent or, for example, carva filter having the shape of an hourglass, a half-hourglass or of a spherical segment. These, however, do not represent a bell shape, but rather are all devices which widen at least at one end like a cone. WO03/075799 also merely discloses an endovascular stent implant in the shape of a bell base, this device being provided with leg-type extensions, therefore likewise making it impossible to recognize a bell shape. These devices only serve to reinforce a vessel. WO01/72239 A2 in turn discloses an implant having an hourglass shape and being formed by cutting out of a tube. Use for recanalizing of organ paths or vessels is not disclosed in this specification, and the hourglass-shaped implant is also unsuitable for such use, especially owing to its centrally constricted shape. US2002/0007222 A1 discloses reinforcing structures for implantation in vessels, said reinforcing structures or stents having a bulging central region and flared end regions, but no bell shape with only one widened distal end and one constricted proximal end and a region disposed thereinbetween which is narrowed relative to the widened distal end.

Constricting the proximal end allows it to be held particularly well in a catheter. The constricted proximal end of the stent may advantageously also be provided with a sleeve element, in order to reliably prevent inadvertent widening of said proximal end and to allow satisfactory attachment to the catheter. Opening of the proximal end and the risk of a section of the object to be compressed entering the stent can likewise be prevented reliably.

The inventive stent is preferably attached at one end to the (carrier) catheter. The remaining body of the stent can be expanded, but preferably not be completely detached from the catheter. This makes it possible to remove the stent from the site of implantation quickly and without problems. In contrast to this, the stents and devices of the prior art as previously described are always completely released from the catheter and can therefore not be removed again, or at least not without difficulty, from the site of implantation within the patient.

Instead of providing a sleeve element and attaching the stent to the catheter, one or more wire-like attachment elements, in particular single wires or a stranded wire, or a plurality of stranded wires where required can be provided for attachment of the stent. They are also fastened so securely to the stent as to permit fast and simple removal of the stent from the site of implantation. Preferably, the proximal end of the stent is formed of at least partly twisted loops which are passed out in particular of the reticular structure of the stent. The loops can be seized by the wire-like attachment element(s), and the wire-like attachment element(s) can be inserted into a catheter. Holding the stent at the site of implantation is accomplished more easily with the wire-like attachment elements than with a stent fixed to the catheter, since the wire-like attachment elements are more pliable and therefore able to adapt to the shape of the organ path. For later removal, the stent only needs to be pulled in the proximal direction at the wire-like attachment elements. The stent which is constricted at its proximal end by the loops and wire-like attachment elements then follows the movement of the wire-like attachment elements for displacement or removal of the stent.

In one embodiment, all of the loops—in another one also only part of the loops—can be held together by a wire-like attachment element. In lieu of a separate wire-like attachment element or a plurality of separate wire-like attachment elements, at least one at least partly twisted loop from the reticular structure of the stent can be longer than the other loops and threaded through the latter to form a wire-like attachment element for the stent. It proves particularly advantageous here to provide the loop designed to form a wire-like attachment element with a sleeve element in the region between its twisted section and the section threaded through the adjacent loops, for the purpose of stabilization of the connection. Preferably, both ends of the loop are pulled through the sleeve element to create an appropriately stable connection. The loop designed to form a wire-like attachment element can be closed or open at its end, with said proximal end of the loop moreover being passed outside the body in order to be able to move the stent at the site of implantation or place it there. The proximal part of the loop designed to form a wire-like attachment element can either be introduced directly into a catheter after threading through the adjacent loops, or can be formed anew into nooses or loops prior to insertion into the catheter in order to ensure even better attachment to the proximal end of the stent.

It is preferred for a region disposed between the distal and proximal ends of the at least one stent to be narrowed relative to the opening width of the distal end and for a section disposed between the narrowed region and the constricted proximal end to be widened relative to the narrowed region. By providing the narrowed region between the widened proximal section and the widened distal end, the object to be compressed can firstly be held particularly well and secondly be pushed into this centrally narrowed region, the compression process therefore also being enhanced.

Preferably, the stent has a reticular structure and/or a multiplicity of openings with an opening width which is smaller than the dimensions of the object to be compressed. Particularly preferably, the stent is made of a braided material and/or woven material and/or scrim, in particular a wire braid and/or woven wire material and/or wire scrim. Alternatively, the at least one stent may consist of a tube which is slotted at least along part of its length. By providing a large number of openings or a reticular structure, fluid can be expressed from the occlusive object to be compressed and eliminated on the inside of the stent. However, solid constituents of the object remain on the outside of the stent in between the latter and the wall of the cavity or organ path or vessel. These solid constituents can be eliminated either after removal of the stent from the cavity or organ path or vessel by a body fluid, blood in particular, appropriately passing therethrough. Alternatively, or in addition, suctioning off of the solid constituents of the occlusive object to be compressed can be provided. To this end, a suction device for suctioning off solid constituents of the object to be compressed or parts of the object is preferably provided, in particular a cannula or suchlike tubular device, which can be guided adjacent to the at least one stent deployed in the cavity, organ path or vessel and operated at subatmospheric pressure. The solid constituents of the object or, where appropriate, smaller parts separated off the object can then be removed from the human or animal body via such a suction device.

The material of the at least one stent is preferably provided with a coating, in particular a biocompatible surface coating, heparin, a carbonization of nitinol, a nanotechnological coating, radiopaque particles, a coating releasing an active substance, an in particular microporous biotechnological or other coating. Dissolution of the object to be compressed can be enhanced even further by provision of such a coating. By providing a coating which roughens the surface of the stent, better holding of the object to be compressed by the stent will also be made possible. However, attention is preferably paid here to avoiding damage to the wall of the respective cavity or organ path or vessel in the human or animal body where the stent is disposed.

The at least one stent preferably consists of a non-thrombogenic biocompatible shape-memory-effect material, in particular a metal or a metal alloy, in particular a stainless steel or nitinol or another biocompatible material, such as a plastic in particular. Since the stent remains in the human or animal body for at least a few hours to days, use of a biocompatible material proves particularly advantageous in preventing rejection effects and allergic reactions. A shape-memory-effect material is preferably chosen in order to be able to mold the stent in the bell shape, to compress it thereafter and to allow it to open by self-expansion.

It proves to be particularly advantageous for the recanalization procedure to guide the at least one stent, contrary to the teaching of WO02/064065 A2, past one side of the object to be compressed and to press it against the respective wall of the cavity/organ path/vessel only from one side. This can achieve particularly effective recanalization, particularly in the case of pulmonary embolism with occlusive embolus, with only eccentric recanalization of the vessel/cavity/organ path taking place, which imposes less stress on the vessel etc. than circumferential dilation. It is possible to make the original throughflow diameter directly available again. The diameter of the expanding stent is therefore preferably substantially equal to or slightly larger than the diameter of the cavity/organ path/vessel to be recanalized. As a result of this, the stent is capable of exerting constant pressure on the object to be compressed and of separating it into its liquid and solid constituents, even as the object decreases in size.

One variant use of the recanalization device according to the present invention is that of an aortic filter. An ever increasing number of patients require these days treatment for a thrombus. Imaging processes have helped to establish that thromboses are found more frequently in the left atrium and the left ventricle. Especially elderly patients are affected ever more often. The number of patients with cardiac arrhythmias is also on the increase. The thrombosis risk is increased in conjunction with procedures and operations, including in particular during ablation and implantation procedures and use of a heart-lung machine. The number of patients otherwise diagnosed with an increased thrombosis risk, e.g. in association with complicated pregnancies, atrial system defect (ASD), PFO, aneurysms in Chagas' disease, tumors, etc., is also increasing. Here, an aortic filter can be used for the protection of both carotid arteries from thrombosis, i.e. a stroke, and for the protection of both coronary arteries from thrombosis, i.e. a myocardial infarction. Thrombi can be captured and removed, e.g. by wedging between vascular wall and stent and subsequent removal by suction. On use of the aortic filter, attention is advantageously paid to the fact that both the material resulting from filtration and the aortic filter itself are not thrombogenic and that, in particular, no highly hazardous microemboli are formed which in turn might damage the arterial system.

The device can be substantially designed to have the same length as an aortic arch in which it is disposed or is intended to be disposed, for the protection of carotid artery and coronary arteries. Alternatively, the device can be designed to be shorter than an aortic arch in which it is disposed or is intended to be disposed, and can have an end which is slightly widened or not widened at all, for the protection of both carotid arteries. If the device is substantially designed to have the same length as an aortic arch, the flared or widened distal end preferably holds on to the likewise flared section at the end of the aortic arch. If, however, the device is designed to be shorter than the aortic arch, thus ending in the implanted state in the middle within the aortic arch, the distal end may in principle also have a widened design, but it will be equally sufficient to widen the distal end only slightly or not to widen it at all, with appropriate fixation within the aortic arch owing to its curvature usually still being ensured when the device is used as aortic filter.

Figure 3:
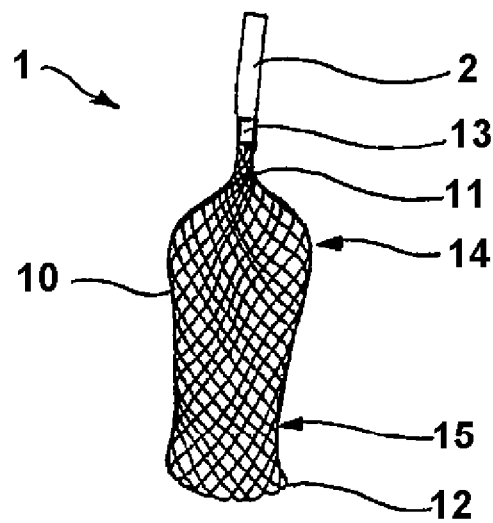
Figure 8:
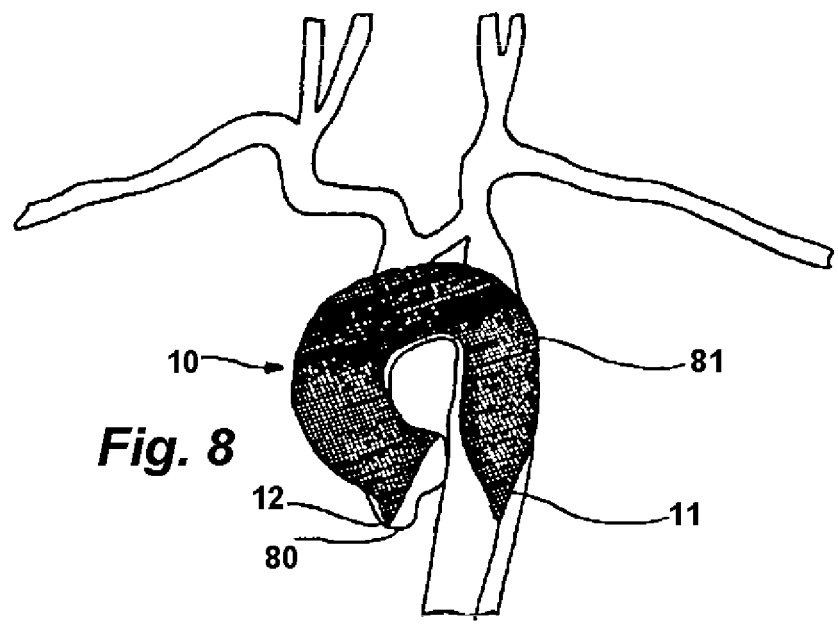
Figure 11:
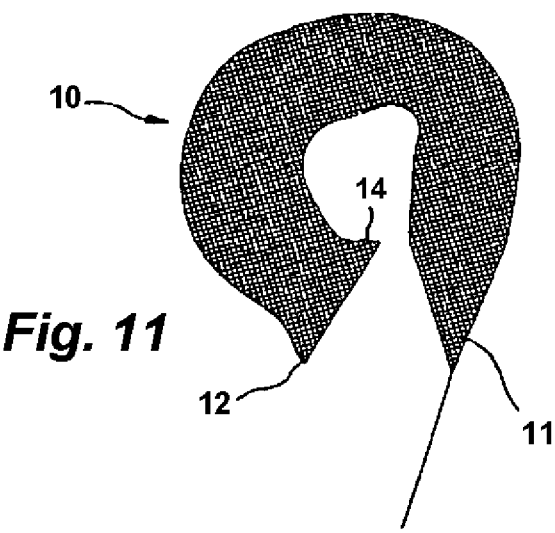
Figure 9:
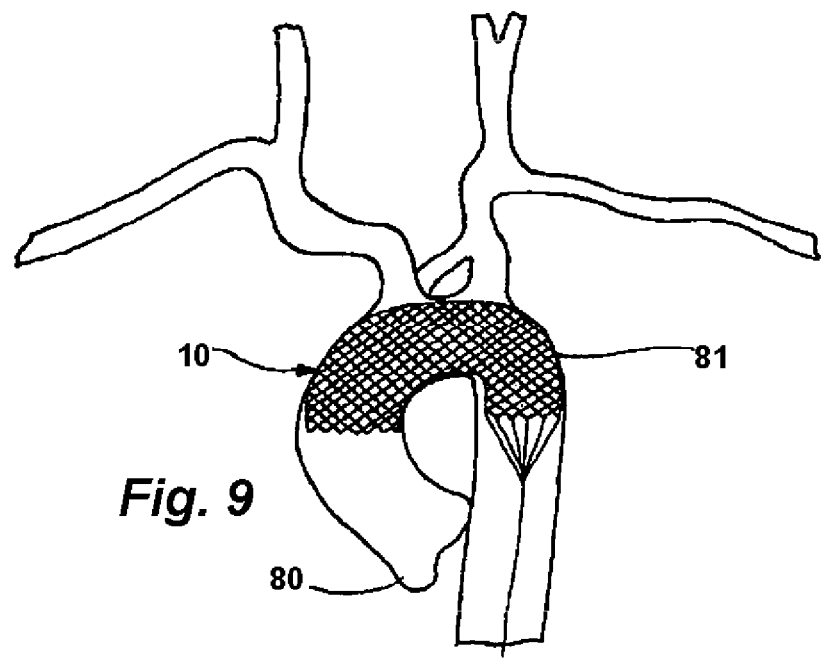
Figure 10:
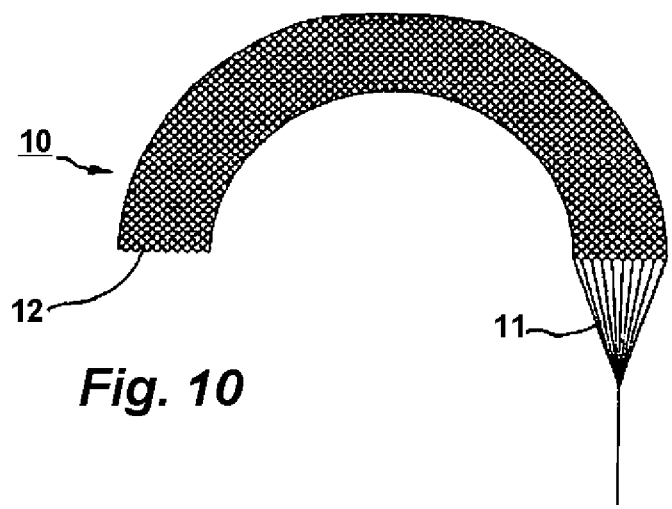

The invention is explained in greater detail below on the basis of exemplary embodiments and with reference to the drawings, in which:

FIG. 1 shows a lateral view of a first embodiment of a device according to the invention having a bell-shaped stent, FIGS. 2a-2f show schematic diagrams of a pulmonary embolism with occlusive embolus and the steps for recanalizing the organ path, FIG. 3 shows a lateral view of a second embodiment of a device according to the invention having a bell-shaped stent, FIGS. 4a-c show detailed views of a first embodiment of a proximal attachment of the stent by wire-like attachment elements, FIGS. 5a-c show a second embodiment of a proximal attachment of an inventive stent via two wire-like attachment elements, FIGS. 6a-c show detailed views of a further embodiment for proximal attachment of an inventive stent by an attachment element with mounted sleeve element and being designed in one piece with a proximal loop, FIGS. 7a-c show a further embodiment of a proximal attachment of an inventive stent via a loop designed to form a wire-like attachment element and passed out of the reticular structure of the stent, with mounted sleeve element, FIG. 8 shows a schematic diagram of a long bell-shaped stent after implantation in an aortic arch, FIG. 9 shows a schematic diagram of a shorter inventive stent after application in an aortic arch, FIG. 10 shows a schematic diagram of the short inventive stent of FIG. 9, and FIG. 11 shows a schematic diagram of the long bell-shaped stent according to the invention of FIG. 8.

FIG. 1 shows a lateral view of a first embodiment of an inventive device 1 for recanalizing an at least partially occluded cavity or organ path or vessel in the body of a human or animal. The device comprises a stent 10 held or attached at its proximal end 11 on a catheter 2. The proximal end of the stent 10 is designed to be constricted or tapers to a very small diameter. In this embodiment, the proximal end 11 is force-fitted into a sleeve 13. This ensures cohesion of the constricted proximal end 11 of the stent. It is moreover possible to use the sleeve as a kind of marker for tracing the deployment procedure and stent position within the respective cavity or organ path or vessel in the body of a human or animal, the sleeve being visible on the X-ray screen. The stent material itself can be radiopaque. The catheter 2 is attached to this sleeve with its distal end and preferably has a diameter such that the sleeve can be held therein, is tightly clamped in there for example. The sleeve clamps the proximal wires of the stent or the proximal end of the stent onto the end of the catheter.

The stent itself is bell-shaped. The bell shape implies that the stent is flared at its distal end 12, is reduced in diameter in the direction toward its proximal end in the region 15, has—starting from the distal end and thereafter—a widened section 14 in the proximal region, with the stent—starting from the widened section 14 in the direction toward the proximal end 11—once again tapering very quickly or being constricted. The diameter of the widened section 14 can be larger than or about equal to that of the distal end 12 of the stent. It is in principle also possible for the widened section 14 to have a slightly smaller diameter than the widened distal end 12. The region 15 disposed between these two widened sections or ends is designed to be narrowed relative to the latter. The region having the smallest diameter is preferably disposed close to the distal end 12, as shown in FIG. 1. This allows particularly good support and holding of the distal end in an organ path or vessel or cavity. In this way, it is at the same time possible to effectively grasp an object to be compressed from the outside and to prevent it from sliding out. This can be seen better in FIGS. 2a to 2f. FIG. 3 shows a less constricted embodiment of a stent of this kind, the latter having a widened region 14 whose diameter is about the same as the diameter of the distal end 12.

FIGS. 2a to 2f show the process of recanalizing an organ path, a pulmonary embolism with occlusive embolus being given as an example. Here, the embolus 3 occludes a branch 5 of a pulmonary artery 4. The embolus is lodged in a branch having a wider diameter, thus rendering the risk associated with such an embolus rather high. The larger the embolus is, the higher is also the risk to the patient of dying, since the sudden increase in flow resistance due to the embolus will cause the circulation within the lungs to collapse. The blood which usually flows to the lung through two pulmonary arteries must then be pumped by the right heart through one pulmonary artery. This may very soon overstress the right heart, which may fail as a result. If the right heart copes with the sudden additional stress, the amount of blood passing through the lungs and reaching the left heart will however be reduced. Since the left heart is capable of pumping on only the amount of blood reaching it, a decreased amount to be pumped will lead to a decrease in the oxygen supply of organs, while the blood upstream of the right heart will accumulate in the veins, which may sometimes lead to shock. It is therefore very important to remove the embolus from the pulmonary artery branch as quickly as possible or to recanalize this branch.

Figure 2A:
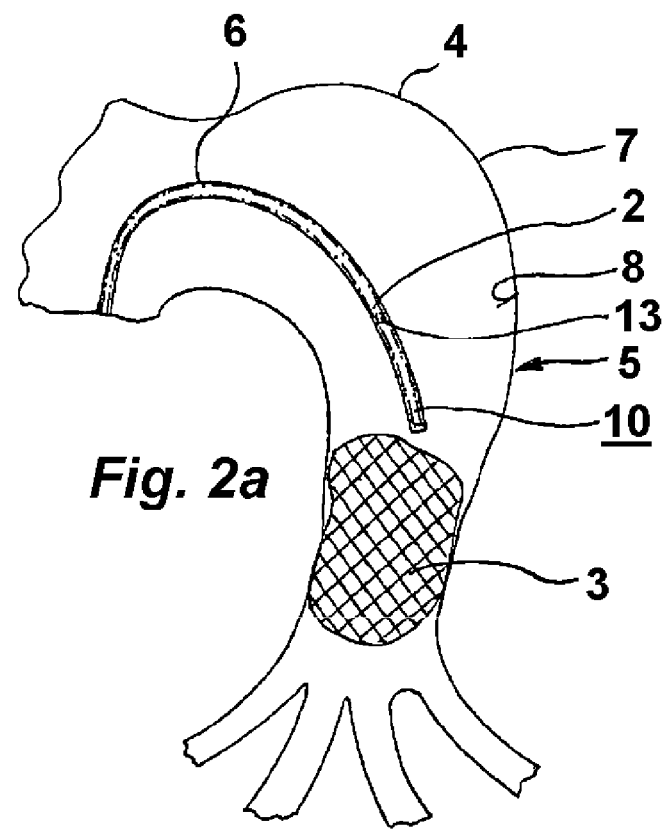
Figure 2B:
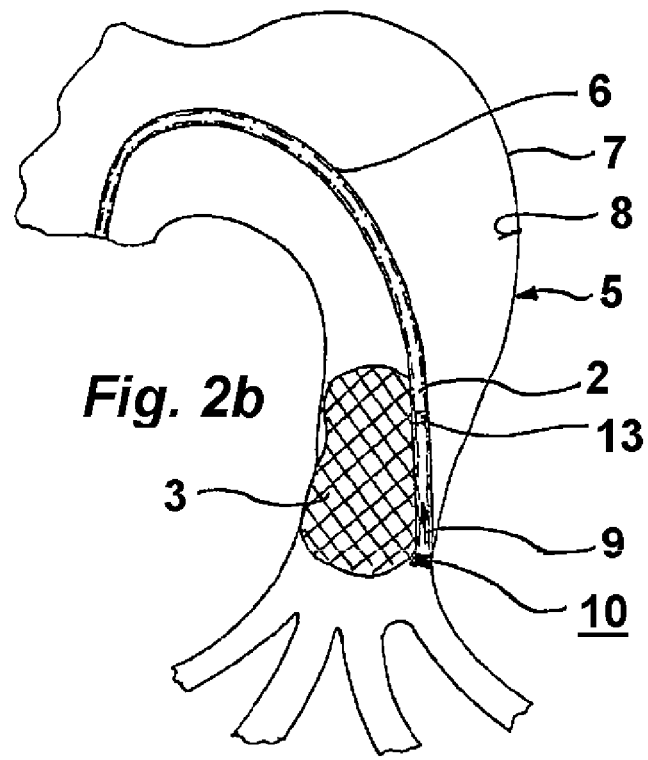
Figure 2C:
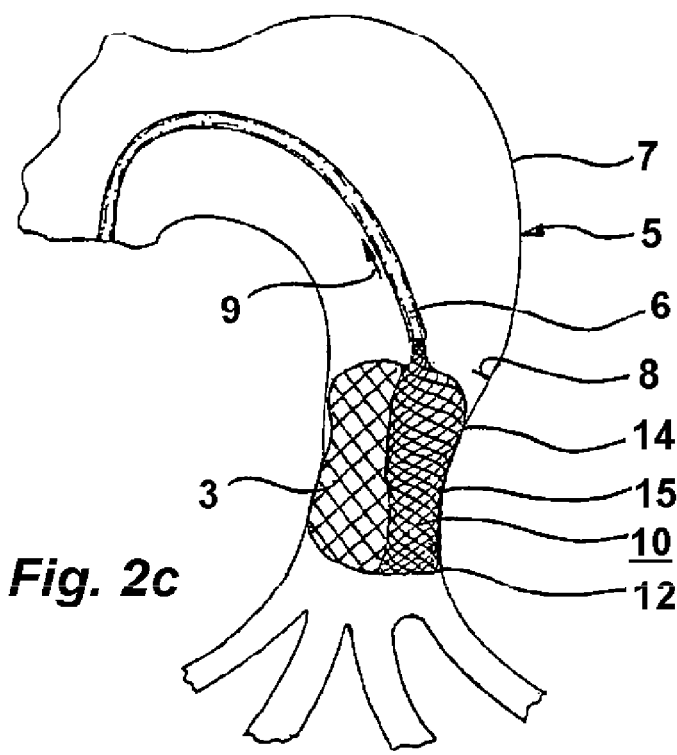
Figure 2D:
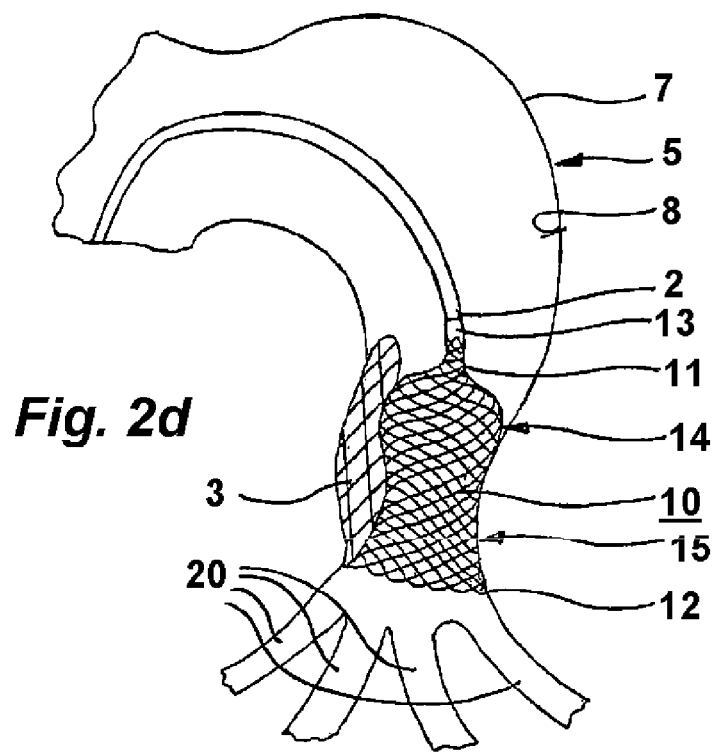

A channel element 6, e.g. a catheter, is therefore introduced into the pulmonary artery 4 in FIG. 2a. The catheter 2 is advanced within the channel element 6 to the embolus 3. The stent 10 is located within the channel element 6, together with the catheter 2, in the compressed state (shown by broken lines in FIGS. 2a to 2f). The embolus 3 is positioned in the pulmonary artery in such a way as to contact the vessel wall 7 on all sides. The channel element 6 is advanced between the vessel wall and embolus, as can be seen in FIG. 2b in particular. It can be introduced therein via a guide wire. Ideally, the channel element 6 is pushed past, rather than through, the embolus, in order to compress it more effectively. It proves advantageous to push the channel element 6 as far as the distal end of the embolus and initiate the deployment process for the stent 10 only there. This will allow the distal end 12 of the stent 10 to move past the distal end of the embolus, thus grasping the embolus distally and pushing it against the inside 8 of the vessel wall 7. The catheter 2 with the compressed stent 10 is advanced through the channel element arranged in parallel to the embolus. The stent 10 is expanded, with controlled retraction of the channel element, as indicated by the arrow 9 in FIGS. 2b and 2c. Since the stent is designed to self-expand, it will push the embolus ever further against the vessel wall 7 once the stent has been pushed out of the channel element 6. FIG. 2d shows the stent in its fully expanded state. Usually the catheter will remain connected to the stent for the duration of the recanalization procedure, which may last for several hours to days. Alternatively, the catheter can be retracted from the lung and only be reintroduced there via the channel element for removal of the stent. In this case, the stent can be provided with a connecting device to facilitate reconnection of stent and catheter 2, for example a hook element on the sleeve 13 and a catch loop on the distal end of the catheter.

As can be seen from FIG. 2d, the bell shape of the stent results in the embolus being pushed against the vessel wall, without the chance of sliding further into smaller downstream arterial branches. And there is no possibility for the embolus to move back into the flow path of the artery at the proximal end of the stent either. The constricted proximal end of the stent 10 will effectively prevent this. Even if a section of the embolus were severed off proximally on compression of the embolus within the region of the widened section 14, it would not reach the smaller pulmonary arterial branches 20, which are also indicated in FIG. 2d. If such a severed-off segment of the embolus reached these pulmonary branches, it might cause an embolism here as well, which cannot be prevented with the prior art stent according to WO02/064065 in particular.

Figure 2E:
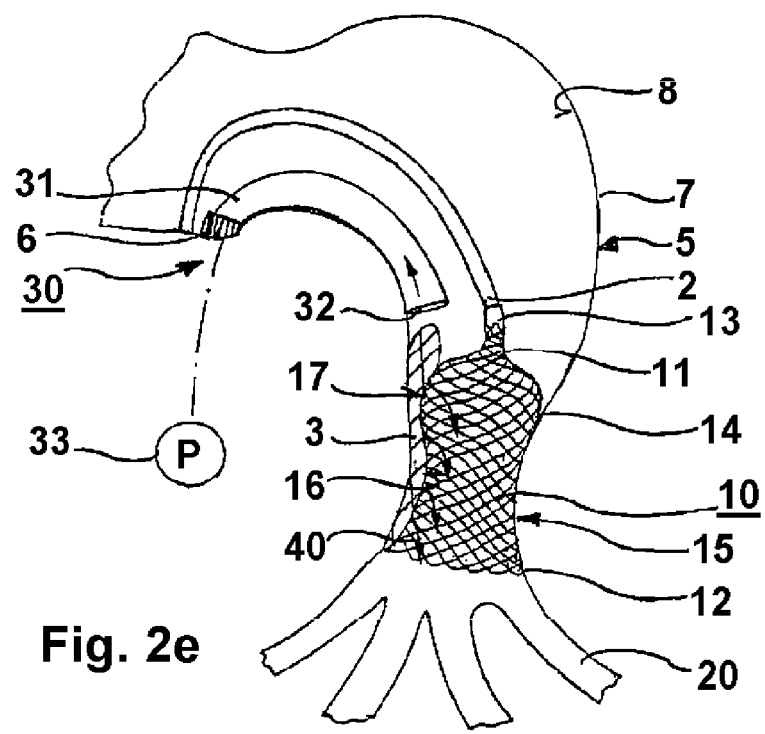

FIG. 2e illustrates the effect of the stent 10. Given that the stent is self-expanding and has a diameter substantially equal to or slightly larger than that of the vessel to be recanalized, it is possible to express the embolus by pressing it against the vessel wall. This means that liquid constituents pass through the meshes of the stent to its inside 16 and solid constituents remain on the outside 17 of the stent. The liquid constituents are then removed by the blood flowing through the stent (arrows 40), whereas the solid constituents are retained between the vessel wall 7 and the outside 17 of the stent. The solid constituents can then be transported away by the blood reasonably easily after removal of the stent. Residues of the embolus on the vessel wall are broken down by endogenous fibrinolyis (physiological lysis agents) in the lung. Drug lysis can be provided in addition to the breakdown of the solid constituents. Alternatively, a suction device for suctioning off the solid constituents can be advanced through a channel element 6 to the region of the embolus 3. In FIG. 2e, the suction device 30 has a cannula 31 which is positioned with its distal opening 32 proximally to the embolus. A pump 33 is arranged proximally to the suction device, to produce a sub-atmospheric pressure, thus making it possible to suction off the solid constituents of the embolus through the distal opening 32 into the suction device or the cannula 31.

Figure 2F:
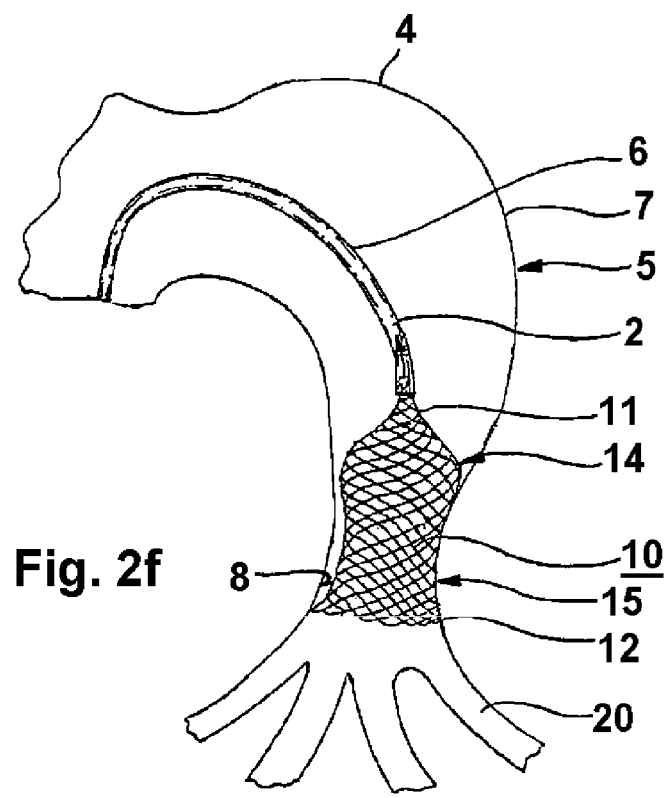

After removal or expression of the embolus, the channel element 6 is pushed past the retained catheter 2, which leads to the compression of the stent, subsequently rendering it possible for the stent to be removed again from the patient's lungs. This process is shown in FIG. 2f. The flared distal end 12 of the stent is compressed last on retraction.

In order to be able to separate the liquid and solid constituents of the embolus through the stent particularly effectively, the latter has a reticular structure. This can be formed by e.g. a woven wire fabric and/or wire scrim and/or wire braid. Alternatively, a tube with cuts can also be provided with such a structure. Of importance here are a number of openings allowing the liquid constituents of the embolus or generally of the object to be compressed to reach the inside of the stent. The openings should not be too large, so that solid constituents can be retained on the outside of the stent between the latter and the vessel wall. The stent can thus have either very fine or relatively coarse reticulation, where the individual mesh opening width ought to be smaller than the smallest diameter of the pulmonary branches. This will prevent solid constituents relodging in the downstream pulmonary branches.

By deploying the stent parallel to the embolus, the latter can be pressed against the vessel wall. The peripheral regions of the downstream pulmonary branches can be supplied again through the stent, thus making it possible to eliminate the adverse sequelae resulting from the deficient supply of these branches and from build-up of a high pressure due to the embolus. Depending on the shape of the object to be compressed, an embolus or thrombus in particular, the stent may remain in the cavity or vessel or organ path to be recanalized in each case for hours up to days. The residence time of the stent within the cavity/vessel/organ path will be shorter in the case of smaller occlusive objects containing large amounts of water than in the case of a large, relatively solid occlusive object. The inventive device for recanalizing is particularly suitable for use in conjunction with pulmonary embolism with occlusive embolus, since a very wide flowthrough path can be opened up here very rapidly. Since an embolus of this kind can be expressed with relative ease, the residence times of the stent within the lungs are moreover relatively short, with no subsequent surgical procedure being necessary for removal of the embolus material; rather, removal of the stent is only minimally invasive, via a channel element.

FIGS. 4a-7c are various embodiments of attachment alternatives for proximal attachment, i.e. in the region of the constricted end, of the stent. Instead of mounting a sleeve element or a sleeve, attachment provided there now is via one or a plurality of wire-like attachment elements. According to FIG. 4a, loops 18 are formed at the proximal end of the reticular structure which are directly connected with the reticular structure 100 of the stent 10 or are passed out of the former. In this connection, two filament sections are in each case passed out as loops at the proximal end of the reticular structure and twisted to form a section 19.

A wire-like attachment element 50 is threaded through the loops 18 and proximally introduced into a catheter 60. It can be guided through the catheter to outside of the body and be fixed there for holding the stent. FIG. 4a depicts the still loose connection between wire-like attachment element 50 and loops 18, whereas FIG. 4b shows a detailed view of the loop of the wire-like attachment element 50 and the various loops 18 of the stent on tightening. The loop 51 formed by the wire-like attachment element 50 can be seen particularly well in the enlarged view in FIG. 4c. It also becomes evident here that the individual loops 18, when bundled, also form a loop through which the loop 51 passes. This produces the constriction of the proximal end of the stent.

In the embodiment of the proximal attachment of the stent in FIGS. 5a-5c, two wire-like attachment elements 52, 53 are provided instead of the one wire-like attachment element. Loops 18 and twisted section 19 are again likewise formed from the reticular structure 100 at the proximal end of the stent. In this embodiment, the wire-like attachment element 52 passes only through half of the loops and threads them together, whereas the other wire-like attachment element 53 passes through the other half of the loops and threads them together. The state of the loops being tied up or gathered up is shown in FIG. 5b and in a detailed view thereof in FIG. 5c. It is evident here that the loops 18 again form one large loop, however, with the two smaller loops of the wire-like attachment elements 52 and 53 engaging. It is in principle possible to provide not just two, but instead more than two such wire-like attachment elements which each engages into and through part of the loops in order to afford constriction of the proximal end of the stent.

FIGS. 6a-7c show a further alternative to FIGS. 4 and 5. No separate wire-like attachment element is provided here, but rather one of the loops, specifically loop 180 is designed to be longer than the other loops 18, again being passed out of the reticular structure 100 of the stent and guided to the proximal end of the stent via a twisted section 19. However, loop 180 projects beyond the actual proximal end of the stent and has its two loop portions 181, 182 threaded through the remaining loops of the stent. After threading through the remaining loops 18, the two loop portions 181, 182 are introduced into the catheter 60 and serve to attach the stent proximally in the same way as the wire-like attachment elements. To provide for stabilization of the attachment, especially since the one loop is threaded through the others and this may otherwise lead to a shift of the reticular structure as well, a sleeve element 70 is mounted onto the loop section 183 disposed between the twisted section 19 and the two loop portions 181, 182. On pulling together the loops by retracting loop portions 181, 182 into the catheter 60, the organized pulling together the stabilization by the sleeve element 70 can be seen particularly well also in FIG. 6b and the detailed view in FIG. 6c. Stabilization via the sleeve element 70 is effected in a similar fashion in the embodiment of FIG. 7a-c, in this embodiment the two loop portions 181, 182 first being laid into further loops 184, 185 before being introduced into the catheter 60, which on pulling together of the loops 18 results in the double enlacement shown in FIGS. 7b and 7c and thus better attachment of the loops 18 in the proximal region.

FIGS. 8 and 11 each show a long inventive stent being used as aortic filter. In FIG. 8, the aortic arch is indicated in the background, in FIG. 11, the inventive stent is depicted without the aortic arch. The distal end 12 of the stent 10 can here attach to the evaginated end 80 of the aortic arch 81. As can be seen particularly well in FIG. 8, the stent fills the aortic arch almost completely after implantation thus making it possible to achieve good filtering performance by pushing undesirable particles against the walls of the aortic arch. An aortic filter of this kind can be used particularly advantageously for patients at a high acute risk of infarction, especially in patients diagnosed as having a thrombus. Most patients are diagnosed as being at an acute high risk of a thrombus in the left auricle of the heart. An inventive stent can be employed in these patients particularly well and effectively for filtering. With an aortic filter of this kind it is possible to help not only freshly operated patients but also PFO patients suffering from a massive venous thrombus. Patients with congenital or dilated heart defects can be treated particularly well with such an aortic filter as well. It is particularly preferred for such temporarily implanted filters, i.e. filters which will be removed again after a certain time, to be implanted together with anticoagulant drugs which can also be applied to the stent itself, as previously stated.

Such an aortic filter is used primarily in embolus prevention for the protection of the coronary arteries (heart) and the carotid artery (brain). It is at the same time used as a thrombectomy system for the protection of the descending aorta from thrombi.

Instead of providing a long stent extending as far as to the evaginated end of the aortic arch it is also possible to provide a shorter stent, as shown in FIGS. 9 and 10, for example. The respective stents extend only in a 180° arc along the most curved part of the aortic arch. In each case the distal end of the short aortic filter stent is substantially not of flared design. Notwithstanding, a flared or widened section 14 can be provided here as well. However, it will likewise be sufficient to provide only a uniformly straight end there, provided the length and shape of the stent prevents unwanted movement thereof at the implantation site.

As can be seen from FIGS. 8-11 as well, the proximal ends 11 are each held by a wire-like attachment element or loop portions 181, 182. In the embodiment of FIG. 11, the reticular structure extends to the proximal tip, whereas in the embodiment of FIG. 10, long loops are formed and held together proximally. Any desired intermediate stages can be formed here as well, attachment via a sleeve 13 and an appropriate catheter 2 as a matter of course again being possible.

In addition to the embodiments of a device for recanalizing a cavity, organ path or vessel in the body of a human or animal described above and depicted in the figures, numerous other embodiments can be formed, each of which provide a bell-shaped stent. The shape of the stent can in particular be adapted to the shape of the cavity or organ path or vessel. Sometimes, shorter stents with a larger opening diameter may be more suitable, at other sites of use, narrower longer stents may be more advantageous. In each of these embodiments, one end of the stent is of a widely flared and open design, whereas the opposite end is designed to be substantially closed and constricted, with another widened region being provided adjacent to this constricted end in order to ensure particularly good attachment within the cavity or organ path or vessel in the body of a human or animal.

LIST OF REFERENCE NUMERALS 1 device
2 catheter
3 embolus (blood clot)
4 pulmonary artery
5 pulmonary artery branch
6 channel element
7 vessel wall
8 inside
9 arrow
10 stent
11 proximal end
12 distal end
13 sleeve
14 widened section
15 constricted region
16 inside
17 outside
18 loop, proximal
19 twisted section
20 pulmonary branches 30 suction device
31 cannula
32 distal opening
33 pump
40 arrow
50 wire-like attachment element
51 loop
52 wire-like attachment element
53 wire-like attachment element
60 catheter
70 sleeve element
80 evaginated end of the aortic arch
81 aortic arch
100 reticular structure
180 loop
181 loop portion
182 loop portion
183 loop section
184 loop
185 loop

What is claimed is:

1. A device for rechanneling a cavity, organ, path, or vessel which is at least partially occluded by at least one compressible occlusive object, such as a thrombus or embolus, in the body of a human or animal, comprising:
at least one compressible and self-expanding stent having a reticular structure, said stent having a compressed configuration adapted for positioning within a lumen, and having an expanded configuration;
said stent having a hollow substantially cylindrical body defined by a sidewall;
said stent having a distal end, and having a proximal end in an engagement with said lumen as a means to maintain a connection with said lumen during insertion into said body and until removal thereof from said body,
said sidewall at said proximal end of said stent in said expanded configuration having an outward taper from a narrowest diameter adjacent to engagement with said lumen, to a wider second diameter at a widened proximal portion of said sidewall;
said sidewall at said distal end having an inward taper from a larger diameter distal end for a distance toward said widened proximal portion;
said inward taper defining a recess in said sidewall, said recess having a smaller diameter than said distal end and said widened proximal portion;
said stent sidewall formed entirely in a reticular structure having a multiplicity of openings therein, said stent in said expanded configuration sized to exert and expanding force to opposing sides of a cavity, organ, path, or vessel in which it is situated in an as-used position;
said openings configured with an opening width which is smaller than the dimensions of the occlusive object to be compressed;
said openings providing means for maintaining substantially full fluid flow through all areas of said sidewall thereby minimizing any impedance of fluid flow therethrough;
said recess providing means for an entrapment of said occlusive object and a concurrent compression of said occlusive object, when said stent is in said expanded configuration in said as-used position in between said occlusive object and a said opposing side surface of said cavity, organ path or vessel;
said entrapment providing means for prevention of a repositioning of said occlusive object within said cavity, organ, path, or vessel; and
said fluid flow through said openings providing means for a fluid rechanneling through said stent sidewall in said as-used position;
wherein:
said stent is deliverable with a catheter and said device further comprises a suction device operable to suction off solid constituents of the occlusive object to be compressed or parts of the object at subatmospheric pressure, the suction device comprising a cannula or tubular device that is positionable adjacent to the stent when the stent is deployed in said cavity, organ, path or vessel;
said device further comprises an attachment to said stent, said attachment formed from one or more wire-like attachment elements comprising single wires or a stranded wire;
a proximal end of said stent is formed of a plurality of partly twisted loops that are passed out of said reticular structure of said stent, said partly twisted loops comprising at least one relatively long partly twisted loop and at least one relatively short partly twisted loop, wherein said at least one relatively long partly twisted loop is threaded through said at least one relatively short partly twisted loop to form one or more wire-like attachment elements for said stent; and
at least one of the partly twisted loops is held together by said one or more wire-like attachment elements.

2. The device as claimed in claim 1, further comprising a sleeve engaged at said proximal end.

3. The device as claimed in claim 1, wherein substantially all said stent sidewall is made of a braided material, woven material, scrim, or a combination thereof.

4. The device of claim 3, wherein substantially all of said stent sidewall is made of a wire braid, a woven wire material, a wire scrim, or a combination thereof.

5. The device as claimed in claim 1, wherein the stent consists of a tube which is slotted at least along part of its length.

6. The device as claimed in claim 1, wherein the stent is formed of a material having a biocompatible surface coating selected from the group consisting of heparin, a carbonization of nitinol, a nanotechnological coating, radiopaque particles, a coating releasing an active substance, a microporous coating, and a biotechnological coating.

7. The device as claimed in claim 1, wherein the stent is formed of a biocompatible material selected from the group consisting of metal, metal alloy, plastic, and combinations thereof.

8. The device as claimed in claim 7, wherein said stent comprises stainless steel, nitinol, or a combination thereof.

9. The device as claimed in claim 1, wherein at least one of said diameter of said distal end and said second diameter is substantially equal to or slightly larger than the diameter of the cavity, organ path or vessel to be rechanneled.

10. The device as claimed in claim 1, wherein at least one of the partly twisted loops is configured to form a wire-like attachment element that is closed at its end.

11. The device as claimed in claim 10, wherein the at least one of said partly twisted loops comprises a twisted section and a section threaded through at least one adjacent partly twisted loop, and includes a sleeve element in a region between the twisted section and the section threaded through the at least one adjacent partly twisted loop.

12. The use of the device as claimed in claim 1 as an aortic filter.

13. The use as claimed in claim 12, and configuring the device substantially to have the same length as an aortic arch in which it is disposed, for the protection of carotid artery and coronary arteries.

14. The use as claimed in claim 12, wherein the device is configured to be shorter than an aortic arch in which it is disposed and has an end which is slightly widened or not widened at all, for the protection of both carotid arteries.

* * * * *